(12) United States Patent
Sleytr et al.

(10) Patent No.: US 7,125,707 B2
(45) Date of Patent: Oct. 24, 2006

(54) USE OF SECONDARY CELL WALL POLYMER OF PROCARYOTIC MICROORGANISMS

(75) Inventors: Uwe B. Sleytr, Vienna (AT); Margit Sara, Ganserndorf (AT); Christoph Mader, Vienna (AT); Bernhard Schuster, Vienna (AT); Frank M. Unger, Vienna (AT)

(73) Assignee: Nano-S Biotechnologie GmbH, Vienna (AT)

( * ) Notice: Subject to any disclaimer, the term of this patent is extended or adjusted under 35 U.S.C. 154(b) by 107 days.

(21) Appl. No.: 10/258,803

(22) PCT Filed: Apr. 24, 2001

(86) PCT No.: PCT/AT01/00122

§ 371 (c)(1), (2), (4) Date: Jul. 3, 2003

(87) PCT Pub. No.: WO01/81425

PCT Pub. Date: Nov. 1, 2001

(65) Prior Publication Data

US 2004/0033576 A1 Feb. 19, 2004

(30) Foreign Application Priority Data

Apr. 26, 2000 (AT) ................ A 732/2000

(51) Int. Cl.
*C12N 9/58* (2006.01)
*B01D 61/00* (2006.01)

(52) U.S. Cl. .................................. 435/243

(58) Field of Classification Search ............ 435/243
See application file for complete search history.

(56) References Cited

U.S. PATENT DOCUMENTS 4,752,395 A 6/1988 Sleytr
4,886,604 A 12/1989 Sleytr

FOREIGN PATENT DOCUMENTS

WO WO 89/09406 A 10/1989

OTHER PUBLICATIONS

Sára M. 2001. Conserved anchoring mechanisms between crystalline cell surface S-layer proteins and secondary cell wall polymers in Gram positive bacteria? Trends Microbiol 9: 47-49.*
Sára M et al. 2000. S-Layer proteins. J Bacteriol 182: 859-868.*
Sleytr UB et al. 1999. Bacterial S-layers. Trends Microbiol 7: 253-260.*
U. B. Sleytr, P. Messner, D. Pum and M. Sára (eds.); *Crystalline Bacterial Cell Surface Proteins, Biotechnology Intelligence Unit*; 1996; R. G. Landes Company, Austin, USA.
U. B. Sleytr, P. Messner, D. Pum and M. Sára; "Crystalline Bacterial Cell Surface Layers (S Layers): From Supramolecular Cell Structure to Biomimetics and Nanotechnology"; *Angew. Chem. Int. Ed*; 1999; 38, 1034-1054.
B. Schuster, U. B. Sleyter, A. Diederich, G. Bähr and M. Winterhalter; "Probing the Stability of S-layer-supported Planar Lipid Membranes", *Eur. Biophys J* 28: 583-580. 1999.
D. Pum and U. B. Sleytr; "The Application of Bacterial S-layers in Molecular Nanotechnology", *Trends Biotechnol* 17:8-12. 1999.

* cited by examiner

*Primary Examiner*—Jean C. Witz
*Assistant Examiner*—Susan Hanley
(74) *Attorney, Agent, or Firm*—Foley & Lardner LLP

(57) ABSTRACT

A compound body can be constructed, using secondary cell wall polymers of prokaryotic microorganisms as bonding agent to anchor a monomolecular lattice to a support, with or without functional groups attached to the lattice. The lattice may be comprised of lipid or crystalline cell surface layer proteins. The support is illustrated by a micro-filtration membrane, a cell surface ultra-filtration membrane (SUM), and a micelle, respectively.

15 Claims, 7 Drawing Sheets

Micelles from molecules type Fig. 5 and S-layer protein and S-layer proteins with built-in functions

Fig.12

USE OF SECONDARY CELL WALL POLYMER OF PROCARYOTIC MICROORGANISMS

The invention refers to the use of the secondary cell-wall polymer of prokaryotic microorganisms and to compound bodies composed of one carrier and one molecular layer.

Crystalline cell surface layers (the so-called S-layers, "S" for surface) are some of the most common outermost cell envelope components of prokaryotic organisms (archaebacteria and eubacteria). S-layers are made up of single protein or glycoprotein species (Mr approx. 50,000 to 2000,000). [Sleytr, U. B., P. Messner, D. Pum and M. Sára. (eds) 1996. Crystalline Bacterial Cell Surface Proteins. In: Molecular Biology Intelligence Unit. Academic Press. R. G. Landes Company. Austin, USA; Sleytr, U. B., P. Messner, D. Pum and M. Sára. 1999. Crystalline Bacterial Cell Surface Layers (S-layers): from Supramolecular Cell Structure to Biomimetics and Nanotechnology. Agnew. Chem. Int. Ed. 38:1034–1054; Sleytr, U. B. and T. J. Beveridge. 1999. Bacterial S-layers. Trends Mocrobiol. 7(6):253–260.] Isolated S-layer (glyco)proteins of many organisms have the capacity for self-assembly into monomolecular crystalline lattices in suspension, on solid supports (for example, silicon wafers, polymers, metals), on the air-water interface as well as spread-out lipid films and liposomes. S-layers show pores of regular size and morphology. Permeability studies have shown that S-layers demonstrate sharp molecular mass separation limits in the ultra-filtration area. These properties have also led to the use of S-layers in the manufacture of ultra-filtration membranes (specification of the European patent No. 0 154 620 B1).

Comprehensive pilot tests have shown that S-layer (glyco)protein of numerous Bacillaceae can recrystallize on spread-out lipid films (for example, phospholipids, tetraetherlipids and other amphiphilic molecules). For this to happen, the lipids are first spread on the air-water interface in a trough according to the Langmuir-Blodgett technique to form a monolayer. It can be advantageous for the recrystallization of S-layer (glyco)proteins on the lipid film that the spread-out lipid film is placed between barriers at a defined spreading pressure. To recrystallize the S-layer (glyco)proteins on the spread-out lipid film, the dissolved S-layer (glyco)proteins are inserted into the subphase where they reach the spread-out lipid film either by diffusion or active mixture of the subphase. The pH-value, ionic strength and ionic composition of the subphase can then influence the recrystallization behavior of the S-layer (glyco)proteins. [Sleytr, U. B., P. Messner, D. Pum and M. Sára. (eds) 1996. Crystalline Bacterial Cell Surface Proteins. In: Molecular Biology Intelligence Unit. Academic Press. R. G. Landes Company. Austin, USA; Sleytr, U. B., P. Messner, D. Pum and M. Sára. 1999. Crystalline Bacterial Cell Surface Layers (S-layers): from Supramolecular Cell Structure to Biomimetics and Nanotechnology. Agnew. Chem. Int. Ed. 38:1034–1054; Sleytr, U. B. and T. J. Beveridge. 1999. Bacterial S-layers. Trends Mocrobiol. 7(6):253–260.]

The recrystallization in the form of a closed monomolecular S-layer comes from nucleation seeds (crystallites). The singular crystalline S-layer domains grow until they meet each other and unite into a contiguous layer. During the recrystallization of the S-layers, bilayers could also form depending on the selected conditions. In these bilayers, the single layers can bind with their inner or outer sides. Pilot tests have shown that S-layer-supported lipid films demonstrate significantly higher mechanical stability as "naked" lipid films. Further pilot tests have shown that the recrystallization of an S-layer does not affect the functionality of lipid membranes. During the build-up of a contiguous associated S-layer, the specific conductivity and specific capacitance of lipid membranes do not change significantly. Sleytr, U. B., P. Messner, D. Pum and M. Sára. 1999. Crystalline Bacterial Cell Surface Layers (S-layers): from Supramolecular Cell Structure to Biomimetics and Nanotechnology. Agnew. Chem. Int. Ed. 38:1034–1054. [Schuster, B.; U. B. Sleytr, A. Diederich, G. Bähr and M. Winterhalter. 1999. Probing the stability of S-layer-supported planar lipid membranes. Eur. Biophys. J. 28:583–590; Pum, D. and U. B. Sleytr. 1999. The application of bacterial S-layers in molecular nanotechnology. Trends Biotechnol. 17:8–12]. Functional molecules can build up before and after the recrystallization of S-layers in the lipid membranes. These functionality studies were done using voltage clamps and black-lipid membrane technology. [Schuster, B., D. Pum and U. B. Sleytr. 1998. Voltage clamp studies on S-layer-supported tetraether lipid membranes. Biochim. Biophys. Acta 1369: 51–60; Schuster, B., D. Pum, H. Bayley and U. B. Sleytr. 1998. Self-assembled α-hemolysin pores in an S-layer-supported lipid bilayer. Biochim. Biophys. Acta 1370: 280–288]. Using the example of α-hemolysin (α-HL), it could be shown that heptamer pores (comprising 7 identical transmembrane pores made of α-HL molecules) build up only when the pore-forming molecules are raised from the lipid side. Because of the molecular filtering action of the S-layer lying in the ultra-filtration area, however, the α-HL molecules do not penetrate the S-layer lattice to reach the lipid membrane. On the other hand, it was shown that smaller molecules (e.g., ionic channels such as valinomycin) are raised from both sides, integrate into the lipid membrane and, as a consequence, can be measured as functional ionic channels using electrophysiological methods. The interaction between monomolecular and bimolecular lipid films (including mixtures with other amphiphilic molecules such as hexadecylamine) and liposomes with S-layer (glyco) protein lattices has so far been investigated using a wide spectrum of biophysical methods. Hirn, R., B. Schuster, U. B. Sleytr and T. M. Bayerl. 1999. The effect of S-layer protein adsorption and crystallization on the collective motion of a planar lipid bilayer studied by dynamic light scattering. Biophys. J. 77:2066–2074. [Schuster, B.; U. B. Sleytr, A. Diederich, G. Bähr and M. Winterhalter. 1999. Probing the stability of S-layer-supported planar lipid membranes. Eur. Biophys. J. 28:583–590; Hianik, T., S. Küpcü, U. B. Sleytr, P. Rybár, R. Krivánek and U. Kaatze. 1999. Interaction of crystalline bacterial cell surface proteins with lipid bilayers in liposomes. A sound velocity study. Colloids Surfaces A 147: 331–339; Mader, C., S. Küpcü, M. Sára and U. B. Sleytr. 1999. Stabilizing effect of an S-layer on liposomes towards thermal or mechanical stress. Biochim. Biophys. Acta 1418: 106–116; Györvary, E., B. Wetzer, U. B. Sleytr, A. Sinner, A. Offenhäuser and W. Knoll. 1999. Lateral diffusion of lipids in silane-, dextran- and S-layer-supported mono- and bilayers. Langmuir 15:1337–1347: Weygang, M., B. Wetzer, D. Pum, U. B. Sleytr, N. Cuvillier, K. Kjaer, P. B. Howes and M. Lösche. 1999. Bacterial S-layer protein coupling to lipids. X-ray reflectivity and grazing incidence diffraction studies. Biophys. J. 76: 458–468; Wetzer, B., A. Pfandler, E. Györvary, D. Pum, M. Lösche and U. B. Sleytr. 1998. S-layer reconstitution at phospholipid monomoleculars. Langmuir. 14: 6899–6909]. It was shown that the recrystallization of an S-layer lattice can have a significant effect on the properties of the lipid film (for example, fluidity) and molecular layout. [Györvary, E., B. Wetzer, U. B. Sleytr, A. Sinner, A. Offenhäuser and W.

Knoll. 1999. Lateral diffusion of lipids in silane-, dextran- and S-layer-supported monolayers and bilayers. Langmuir. 15:1337–1347]. Basically, S-layer-supported lipid membranes correspond to the supramolecular building principle of the cell envelope of those archaebacteria (Archaee) that have only one S-layer as a cell wall component apart from the cystoplasmic membrane. But since isolated S-layer (glyco)proteins of archaebacteria are significantly more difficult to recrystallize on lipid films, the S-layer glyco(proteins) of other prokaryotic organisms (for example, Bacillaceae) are preferable. The manufactured composite S-layer lipid films are then biomimetic structures that are adapted to the cell envelopes of Archaebacteria, etc. and the native components of the Archaebacteria need not be used.

From work and publications of the applicants it is known that the S-layer (glyco-protein) of Gram-positive bacteria can be bonded to the underlying rigid cellular wall layer (the so-called peptidoglycan-containing layer) with very specific reciprocal action taking place. This specific bonding evidently occurs often between the S-layer protein and the so-called secondary cell wall polymers (referred to below in the text as "SCWP"). These polymers are bonded covalently to the matrix of the peptidoglycan layer and can be separated from it (for example, by treating it with HF) and extracted in pure form. From the comparison of amino acid sequences of various S-layer proteins, domains were traced that are responsible for the bonding of the S-layer to the peptidoglycan-containing cellular wall layer, especially the SCWP components.

As is already known from Pum, D. and U. B. Sleytr. 1999. The application of bacterial S-layers in molecular nanotechnology. Trends Biotechnol. 17:8–12 and Sleytr, U. B. and M. Sára. 1997. Bacterial and archaeal S-layer proteins: structure-function relationships and their biotechnological applications. Trends Biotechnol. 15:20–26, the S-layer has a stabilizing effect on lipid membranes. These publications describe procedures where the S-layer proteins in troughs were recrystallized from the subphase on spread-out lipid films or on black lipid membranes.

The principle of SUM-supported lipid membranes [SUM: S-layer ultra-filtration membrane] could also lead completely to new application possibilities for functional lipid membranes. It is considerably simpler to bring a lipid film onto an SUM (for example, by means of the Langmuir-Blodgett or Langmuir-Schäfer method) or to assemble it directly on the film than first to manufacture the lipid film by spreading it on a trough and then to recrystallize the S-layer proteins from the subphase on the lipid film. The use of SUMs would also facilitate the development of new testing methods according to the principle of the voltage-clamp measuring technique as they are required, for instance, in the screening of pharmaceutical substances for their effect on the membrane-integrated or membrane-associated molecules (for example, ionic channels, signal-transmitting molecules).

Moreoever, the voltage-clamp technique is also known: a delicately extracted pipette filled with buffer solution is carefully brought close to a (functional) lipid membrane so that measurable contact ensues. Consequently, the transmembrane functions are determined by electrophysiological means (for example, by measuring the trans-membrane currents). This widely established method, however, cannot be used for parallel studies as such studies are needed for high-throughput screening (testing of many substances in one operational step).

At the present state of science, there are methods for manufacturing composite S-layer lipid films where the S-layer (glyco)protein are recrystallized from a solution on lipid films (for example, Langmuir films, black lipid membranes) in mesoscopic and macroscopic dimensions.

Among other things, the object of the invention is the task to find new ways to stabilize lipid films.

The invention resolves this task by using secondary cell wall polymers for the directed monomolecular bonding of (functional) molecules, preferably molecular layers and/or for the attachment of functional molecules on molecules of a support. In this manner, the specific interactions between one or more domains of the S-layer proteins and the so-called secondary cell wall polymers are used for making supra-molecular structures.

The making of these S-layer membranes is already the subject of a patent issued in many states (see, for instance, specifications of European patent 0154620 B1). Basically, this procedure involves the attachment of S-layer fragments or cell wall fragments of S-layer-supporting Prokaryotes onto porous supports; (preferably) micro-filtration membranes with open-cell, spongiform structure or membranes that were made according to the radiation-damage track technology (for example, nucleopore membranes). After the attachment of a contiguous S-layer position (this can also consist of several individual layers), the S-layer lattices are chemically cross-linked intra and inter-molecularly (preferably with glutaraldehyde). When using glutaraldehyde as a chemical cross-linker, it is preferable to reduce the ensuing Schiff's bases with boron hydride to increase the chemical stability of the S-layer membranes. The S-layer membranes made this way are used as ultra-filtration membranes because of the molecular filtering action of the S-layer lattice. These S-layer ultra-filtration membranes will henceforth be abbreviated to SUMs.

By using SUMS as support for functional lipid membranes (or membranes that consist of other film-building, say, amphiphile, molecules), significant technical and application-related advantages can be achieves in comparison to the aforementioned procedure for recrystallizing S-layers on spread-out lipid films.

The attachment or the creation of (functional) lipid films on SUMS can be done in many various ways:

1. Immersion and/or emersion of the SUMS from a lipid film spread out on a trough (for example, Langmuir-Blodgett or Langmuir-Schäfer technique). While a "functional" lipid membrane can be made by simple immersion or emersion using a spread-out tetraether lipid film, two steps (immersion and emersion sequences) are necessary for phospholipids, for instance.

2. Manufacturing a chemically bonded lipid monolayer on the S-layer lattice where the hydrophobic parts of the amphiphilic molecules stay away from the SUM. The second lipid monofilm is then attached accordingly using the Langmuir-Blodgett or Langmuir-Schäfer technique (see above).

3. Certain functions (for instance, biotinylation, cysteine residues, streptavidine bonding domains) can be built into the S-layer lattices. In this way, the corresponding SUM surfaces can deal with a specific interaction with lipid molecules or other amphiphilic molecules. This is how composite S-layer/lipid membranes are made where the lipid film is bonded to the S-layer (glyco)protein matrix of the SUM according to the repetitively occurring specific bonding position.

4. After the lipid film is attached to the SUM, a covalent chemical cross-linking of head groups of lipid films (or the amphiphilic molecules) occurs with the S-layer matrix. This cross-linking reaction preferably happens after the cross-linking substance permeates through the porous support of the SUM (for instance, through the micro-filtration membranes).

It is advantageous that the secondary cell wall polymers can bind through the respective domains of the functional molecules, preferably the molecular layers and/or molecules of the support. One the one hand, this allows one to pinpoint exactly the functional molecules or molecular layers and, on the other, align them precisely. The secondary cell wall polymers can then bind to the molecules, preferably the molecular layers or molecules of the support, through lectin-like bonds, which also facilitates an exact selection of the domains or epitopes for bonding the molecules or molecular layers to the supports.

A preferred application in the invention involves having the secondary cell wall polymers as the bonding agents between the polymer support structures and the function molecules, molecular groups or molecular layers, where the polymer support structures can be loaded directly with the appropriate functional molecules. The support structures can then be micro-filtration membranes. In addition, the molecular layers can come in the form of monomolecular crystalline protein layers, where, on the one hand, appropriate filters with sharp cut-off can be made because of the crystalline structure of the protein layer and, on the other, these protein molecules, in turn, can be loaded directly or indirectly with functional molecules. The monomolecular crystalline protein layers, in turn, act as a support for a functional lipid membrane, achieving very stable composite structures that, for example, can be used for hyperfiltration and the like. Furthermore, one or more identical or different functional domains can brought onto that side of the monomolecular crystalline protein layers averted from their secondary cell wall polymers, with the protein layers used as mediator for an arranged bonding of other molecules. To achieve special bonding possibilities, the monomolecular molecules can have amphiphile characteristics and consists of hydrophobe chains and hydrophile secondary cell wall polymers. This allows one to control the direction of the attachment to a aqueous or non-aqueous phase. Furthermore, the molecules of the support can be monomolecular crystalline protein layers where the secondary cell wall polymers make up the bonding agents to a functional lipid layer during the formation of an aggregate compound body. The lipid molecules are distanced accordingly from the protein layers in such a way that the lipid layer is firmly bonded to the protein layers. So through functional lipid layers two aggregate compound bodies can then be bonded as mirror images of each other. This allows the build-up of layers according to the so-called sandwich principle. The monomolecular crystalline protein layers can consist of identical or different protein molecules, which make it possible for various bonding domains, charges, functional molecules and the like to be present on the outer layer of the compound body, thus greatly expanding the scope of application.

Finally, the functional lipid layer may have a vesicular structure which, according to its nature, allows artificially adjusted compound bodies.

As already mentioned, the invention also refers to a compound body consisting of a support and a molecular layer which is thus marked in the invention that the molecules of this molecular layer are bonded to the support, in a monomolecular direction, through secondary cell wall polymer chains according to the invention's application. This facilitates the build-up of a precisely structured, precisely defined compound body chemically and functionally.

The secondary cell wall polymer chains can anchor on the support and/or the bonding molecules through a lectin-like bond, where one of the passing domains of the protein molecule attains an appropriate bond. To obtain a stable compound body, monomolecular crystalline protein layers can be bonded on a polymer matrix through the secondary cell wall polymers where these secondary cell wall polymers act as the anchor and the alignment and/or the target distribution. Lipid films or vesicles can also be configured on that side of the monomolecular crystalline protein layers averted from the secondary cell wall polymers, providing additional application possibilities. Furthermore, functional domains can be designated in regular intervals and configurations on that side of the monomolecular crystalline protein layers averted from the secondary cell wall polymers, allowing a targeted attachment of other functional molecules on the protein layers.

To achieve different kinds of bonds or distribution of functional molecules, the functional domains can be provided in different but regular patterns.

Moreover, the secondary cell wall polymers of one monomolecular crystalline protein layer, which preferably is attached directly onto a support, jut out and bond to a functional lipid layer. This produces a stable support layer because of the protein layer directly attached to the support: the lipid layers are bonded to the secondary cell wall polymers free from interactions of the protein layer. Two such protein layers can then bind through the functional lipid layer opposite each other as mirror images, leading to a stable sandwiched compound body. The one protein layer can consist of other protein molecules as the other protein layer so that different bonding relationships, domains and functions can exist on both sides on the compound body.

As a variant of the known voltage-clamp technique described above, the compound body can be configured so that it spans the opening at one end of a small tube. In comparison to the known open pipette, such a small tube equipped with the compound body used in the invention (referred to hereinafter as the SUM tube) can be brought near the spread-out functional lipid membrane much more quickly without disturbing the film. Numerous SUM tubes laid out beside each other can then be used simultaneously, for example, for measurements conducted on functional lipid membranes. Basically, one can conceive of measuring procedures where the first step involves layering all SUM tubes with functional lipid membranes. This could be done by immersing them in a spread-out tetraether lipid film in which, in a preceding step, functional molecules are built in. [Schuster, B., D. Pum and U. B. Sleytr. 1998. Voltage clamp studies on S-layer-supported tetraether lipid membranes. Biochim. Biophys. Acta 1369:5–60]. In the second step, the SUM tubes would be lowered into small vessels (for instance, similar microtiter plates) containing various substances whose effect on the membrane-associated or membrane-integrated functional molecules should be tested. The electrophysiological measurements would then be done according to the classic voltage-clamp technique.

Together with SCWP, SUMS could also serve as support for functional lipid membranes in the macroscopic area. Currently, there are hardly any comparable support layers for the large-surface stabilization of lipid membranes.

Finally, the compound body used in the invention can be used as support for special functional molecules for diagnostics, drug targeting, drug delivery, artificial virus drug screening, high-throughput screening or the like.

With the use described in the invention, vesicular structures can also be created: for example, liposomes or lipid drips (lipid particles) coated with S-layers.

Finally, a micelle composed of hydrophobic self-assembling chains can also be used as support.

The diagram shows an enlarged cross-section of various configurations of the compound body.

Figure 1:
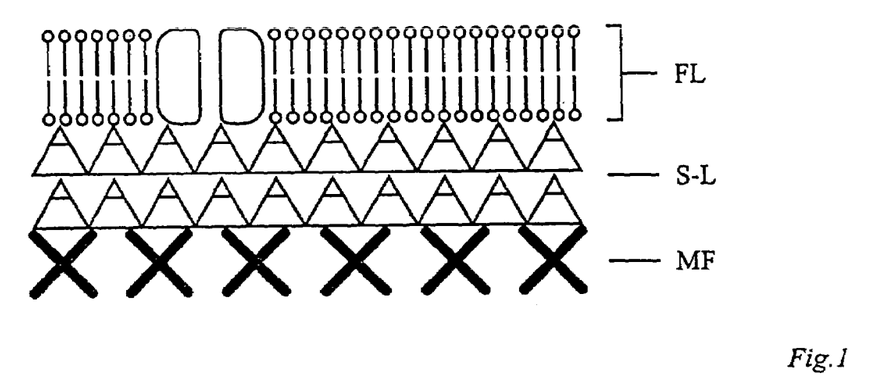
FIG. 1 shows the use of S-layer ultra-filtration membranes.

FIG. 1 shows the basic use of S-layer ultra-filtration membranes with the following abbreviations used in all pictures:
MF: micro-filtration membrane,
S-L: S-layer,
FL: functional lipid membrane, that is, lipid membrane with built-in membrane function, especially transmembrane function (e.g., ionic channel).

Such a configuration is already the state of the art of the applicant's own work.

Figure 2:
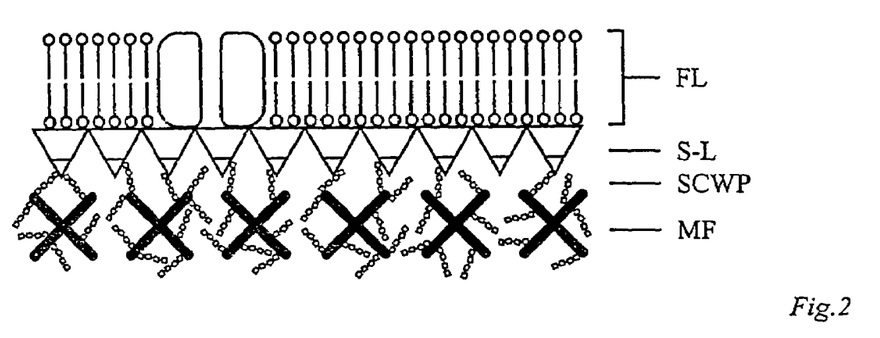
FIG. 2 shows the chemical coupling of the SCWP to another polymer.

FIG. 2 shows the chemical coupling of the SCWP to another polymer and the resulting mixture of these molecules with a polymer usually used for making micro-filtration membranes (with spongiform structure). During the illuviation process in aqueous solutions (e.g., according to the phase inversion procedure), hydrophilic SCWPs should jut out into the aqueous phase while the polymer chains (covalently) bonded to them are anchored in the compact polymer structure.

Basically, one should also think of other possibilities to functionalize the surfaces of polymer structures (films, spongiform or other porous structures) with SCWPs. In all of these procedures the hydrophilic SCWP chains jut out at a sufficient distance from the surface of the polymer structures to allow contact to the corresponding bonding domains of the S-layer proteins.

Besides the polymerization procedure, chemical coupling methods can also be used. For example, reactive groups could be built into one end of the SCWP. These groups can then react with groups on the surface of the polymer structures. Conversely, pre-activated groups can be brought to react with reactive groups on the SCWP.

Figure 3:
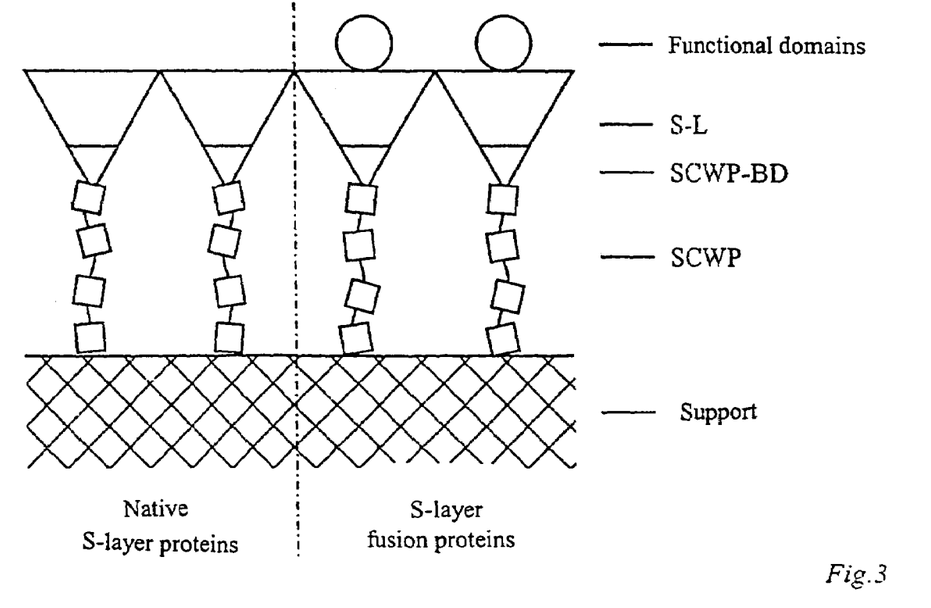
FIG. 3 shows S-layers on the polymer surface functioning with the SCWP.

As shown in FIG. 3, S-layers on the polymer surface functioning with the SCWP can then be recrystallized from a solution of S-layer (glyco)protein. This method would lead to a complete monomolecular S-layer coating of the polymer surface. Since S-layer fusion proteins with built-in specific functions (for example, biotin binding domains of the streptavidin, protein A, protein G, antibody or antigen domains) can be used for the recrystallization besides native S-layer (glyco)proteins, a very uniform functionalization of polymer matrices can be achieved using this method (see above).

Figure 4:
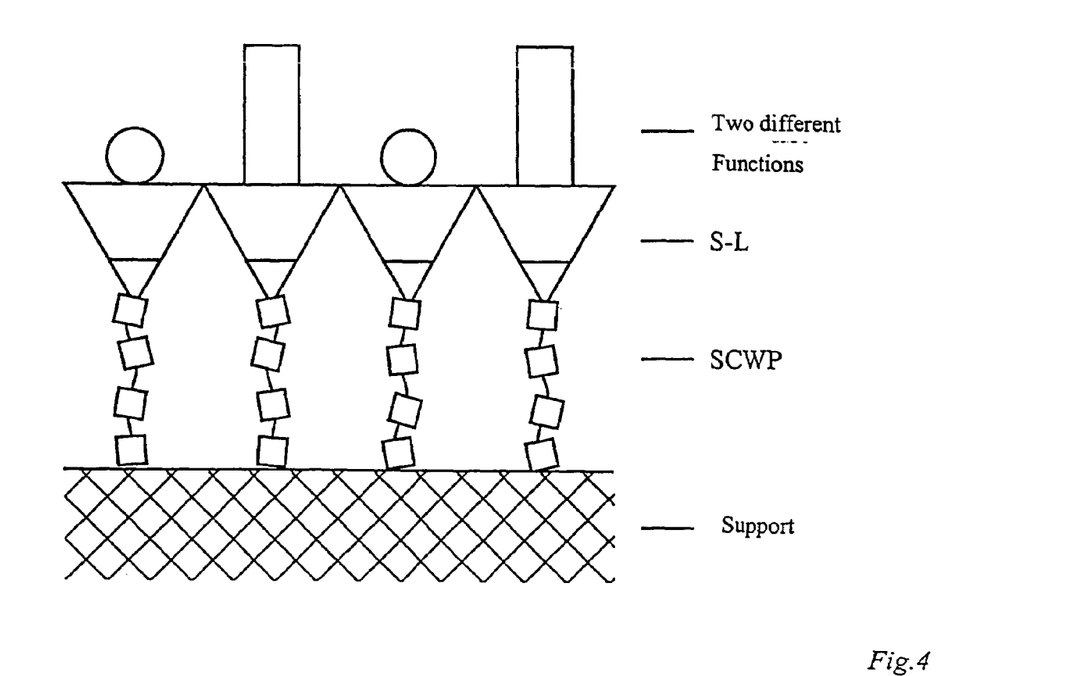
FIG. 4 shows the use of S-layer fusion proteins that are differently functionalized.

With the use of S-layer fusion proteins according to FIG. 4, two or more identical but differently functionalized S-layer proteins could also be used simultaneously. In this manner, a uniform S-layer lattice would build up on the SCWP because of the uniform protein base structure. This lattice, however, would have different bonding positions (functional domains) in discrete intervals (but statistically distributed).

Figure 5:
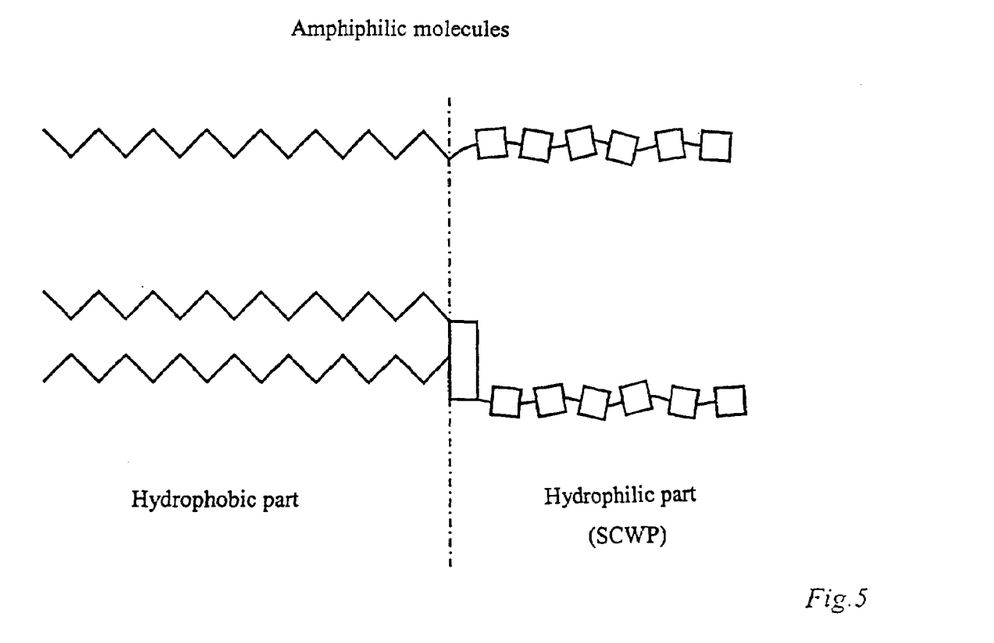
FIG. 5 shows the use of amphiphilic molecules consisting of SCWP and hydrophobic chains.

FIG. 5 shows the use of amphiphilic molecules consisting of SCWP and hydrophobic chains that correspond, for instance, to glycolipids in their molecular structural concept. Similar molecules are also found, say, in the plasma membranes of Archaebacteria (Archaea). The diagram, in particular, shows the making of glycolipid-equivalent molecules.

Figure 6:
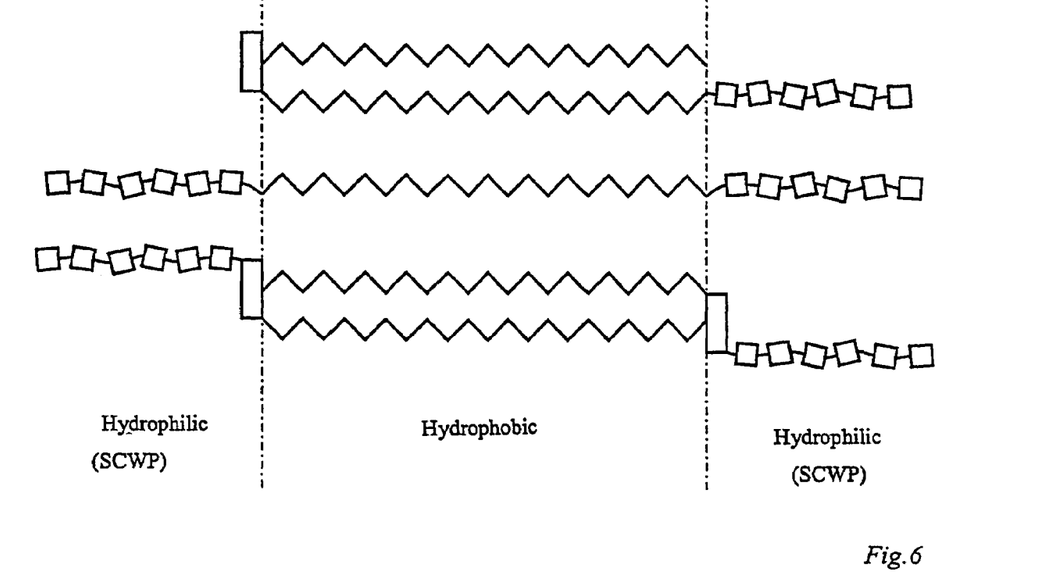
FIG. 6 show the use of molecules with one central hydrophobic part and two hydrophilic domains.

FIG. 6 shows the use of naturally occurring or fully synthetic molecules consisting of one central hydrophobic part and two hydrophilic domains.

Figure 7:
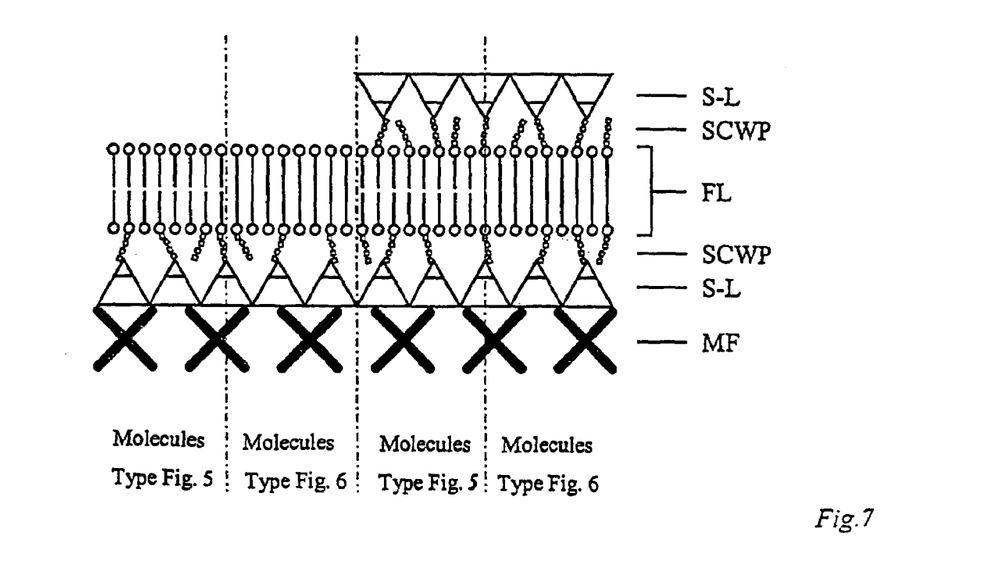
FIG. 7 shows composite SUM/lipid membranes.

FIG. 7 illustrates the use of the molecules shown in FIG. 5 and FIG. 6 for making composite SUM/lipid membranes. The use of the amphiphilic molecules allows wide variation in configuring composite SUM/lipid membranes. The basic possibility to use two different SCWPs that bind to different S-layer proteins deserves special mention.

Figure 8:
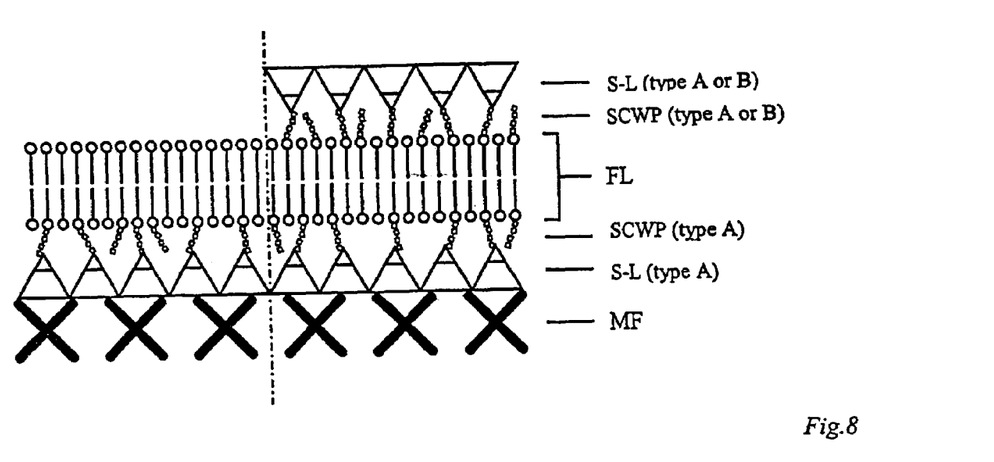
FIG. 8 shows the making of composite S-layer/functional lipid membranes using SCWPs.

FIG. 8 illustrates the making of composite S-layer/functional lipid membranes by using SCWPs. The following abbreviations are used in FIG. 8:
A: S-layer protein type A
SCWP-A: secondary cell wall polymer that binds specifically to type A S-layer proteins,
B: type B S-layer protein
SCWP-B: secondary cell wall polymer that binds specifically to type B S-layer protein.

An S-layer (for example, type A) is first brought on the micro-filtration membrane. Basically, this process corresponds to the above-mentioned procedure for making SUMs. Consequently, a monolayer of amphiphilic molecules (suited for making functional lipid membranes, see examples) is brought on the SUM by using either the Langmuir-Schäfer technique or the Langmuir-Blodgett technique. The monolayer is connected to the SUM by means of the specific interaction of the SCWP part of the amphiphilic molecules with the S-layer with the SUM. This anchoring of lipid monolayers onto S-layers on SUMs led to a significant increase in stability and longevity of functional lipid membranes.

As an alternative to the molecules described in FIG. 5, the molecules specified in FIG. 6 can also be used to make functional lipid membranes where the latter facilitate the making of a functional lipid membrane in one step. By using the molecules shown in FIG. 5, on the contrary, another monolayer of amphiphilic molecules can be applied in a second step. If this outer layer contains amphiphilic molecules with a SCWP part, the exposed SCWP chains can serve as specific bonding positions for another S-layer. This second S-layer can, for example, be recrystallized on the lipid membrane from a solution of S-layer (glyco)proteins. Alternatively, the S-layer can also be recrystallized in the first step on the air-water interface and only then applied to the lipid membrane (say, by immersion).

The supra-molecular layer system shown in FIG. 8 can be done by using uniform or different SCWP-S-layer partners.

The diagram shows examples of type A S-layer and type A SCWP as well as type A S-layer and type A SCWP with type B S-layer and type B SCWP.

To attach lipid membranes on supports, the so-called liposome fusion technique is used multiple times. Under this method, the lipid membrane is offered as a lipid vesicle (so-called liposomes). Preferably the desired funcational molecules are already built into the liposomes. Under appropriate trial conditions, the lipid vesicles open upon contact with the surface of the solid support to finally form a contiguous lipid film.

Figure 9:
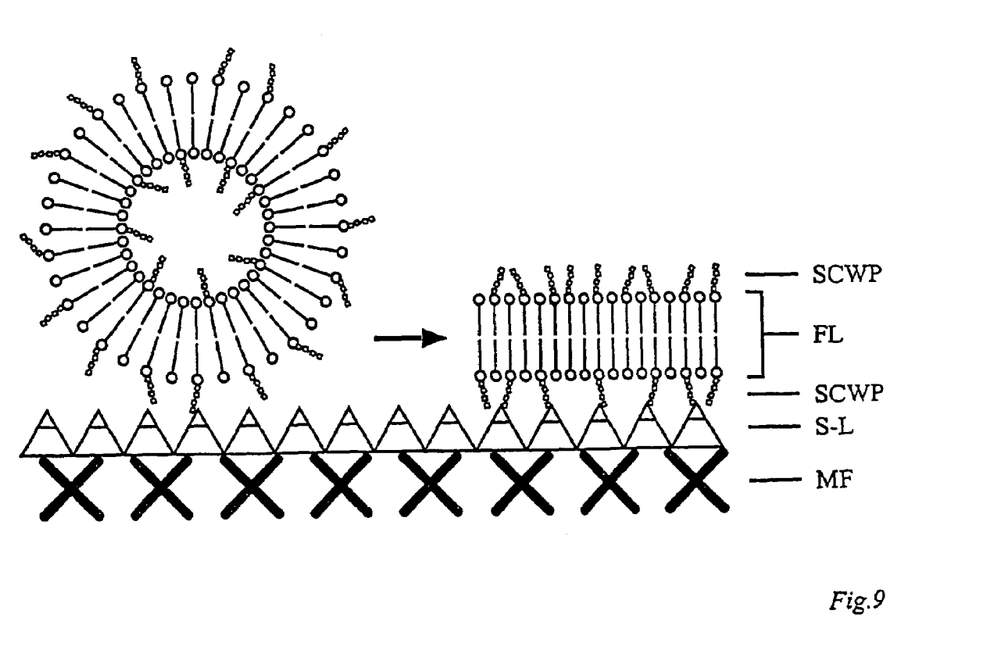
FIG. 9 shows the use of the SCWP system to accelerate vesicle fusion.

As shown in FIG. 9, the SCWP system can also be used, where necessary, to accelerate this vesicle fusion and secure the bonding of the lipid film to the SUM.

Using SUM-supported (stabilized) functional lipid membranes for high-throughput screening.

There are basically two measuring setups:
a) voltage clamp or patch clamp methods
b) black lipid membrane methods In both cases, the use of SUMs should extend the lifetime and thus the usability of functional lipid membranes.

Making SUM Tubes

Figure 10:
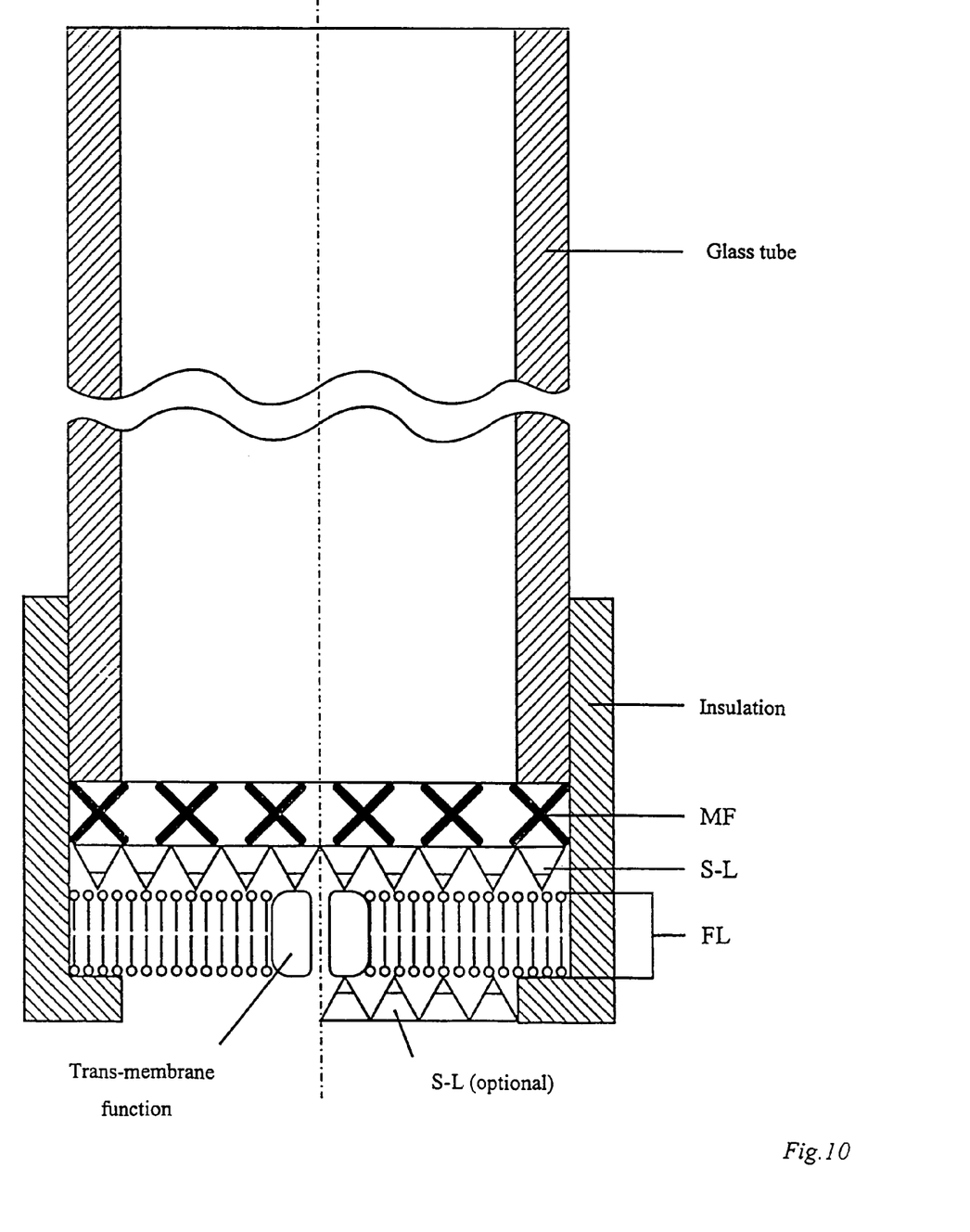
FIG. 10 shows that SU should be mounted at the end of a glass or plastic tube to make a SUM-spanning aperture.
Figure 11:
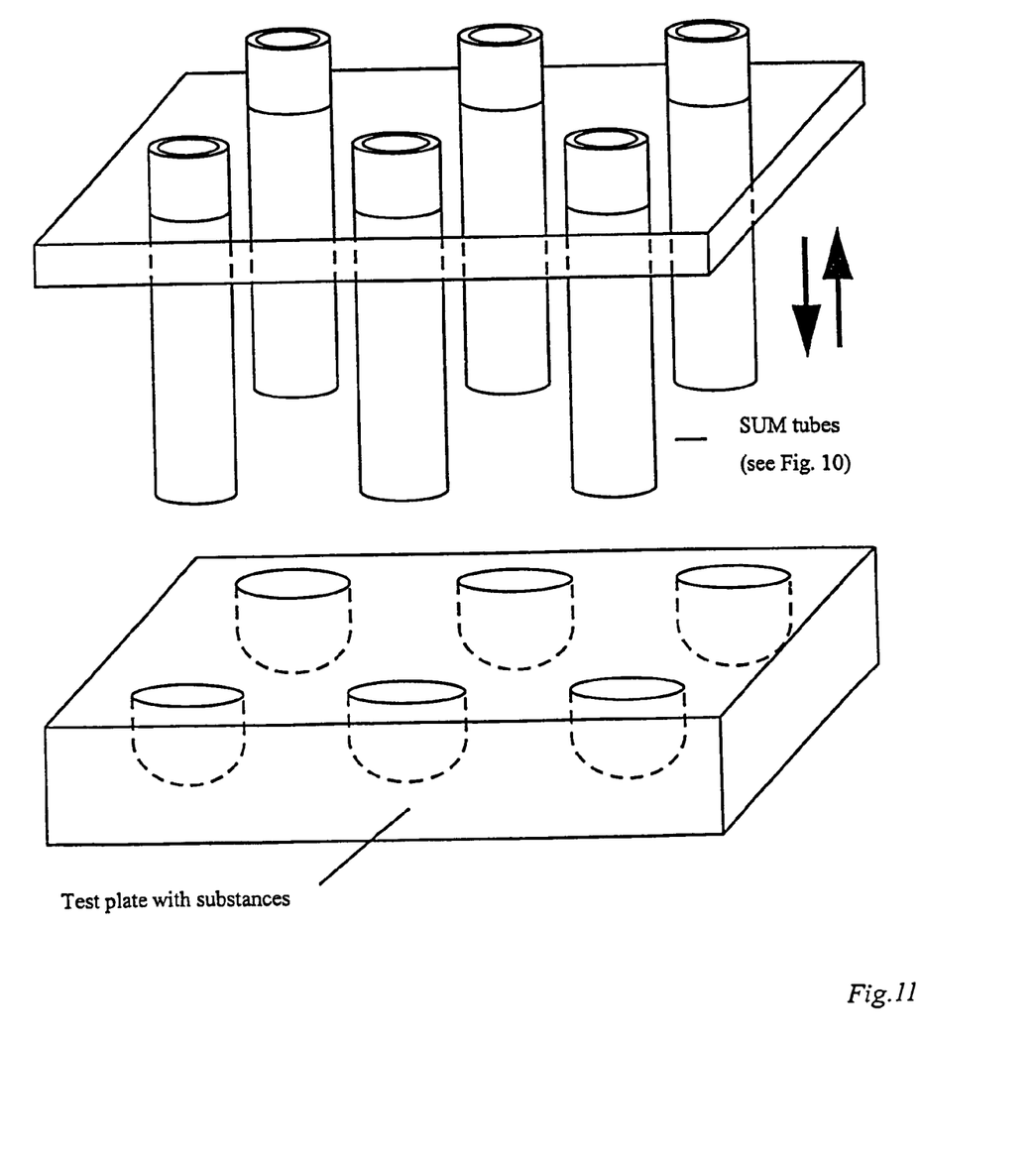
FIG. 11 shows SUM tubes, separately or together.
Figure 12:
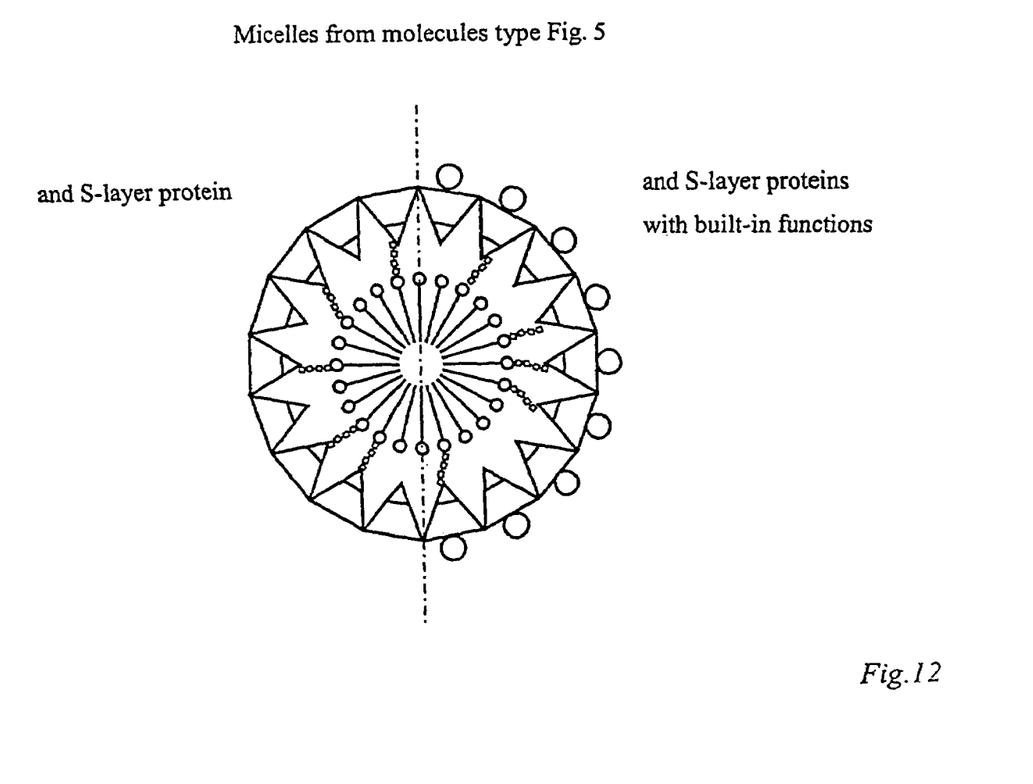
FIG. 12 shows micelles with S-layer proteins.

As shown in FIG. 10, the SUM should be mounted at the end of a glass or plastic tube resulting in an SUM-spanning aperture. In principle, this part would correspond to the opening of a patch clamp or voltage clamp pipette, with the difference that the (functional) lipid membrane does not span over the pipette opening but is supported by the SUM. Mounting the lipid membrane and its functioning could follow the methods already described above.

Another advantage in using SUM tubes is that after applying the lipid membrane another S-layer could be applied by deposition or recrystallization (see FIG. 7 and FIG. 8). This additional S-layer would fulfill a (further) stabilizing and protective function. In this context, one has to recall the sharp molecular cut-off of the S-layers.

After the lipid membranes are applied to the SUM, or before or after the possible recrystallization of another S-layer, an intermolecular and/or intramolecular chemical cross-linking of the S-layer (glycoprotein) matrix and of the lipid film can occur. For this to happen, appropriate cross-linkers must be applied to the aqueous phase.

The SUM tubes can be used either separately or in groups (see FIG. 1). A group configuration allows the application of the lipid membranes in one operating step and, consequently, the performance of parallel measurements in any number of vessels containing various substances whose effect on the functionalized membranes should be tested. When using SUM tubes, active substances could also be added directly to the glass tubes filled with buffer solutions or water. Furthermore, where necessary, the environmental conditions (e.g., ionic strength, ionic composition, pH-value, temperature) in the tubes and, separately, in the vessels where they are immersed could also be altered without possible pressure fluctuations affecting the integrity of the functional lipid film. This same increased stability of the SUM-associated lipid membranes mentioned in the outset as compared to the pressure changes merits special mention in applications for the invention. The advantages mentioned above can also be applied directly to the test setups of black lipid membranes.

In conjugates consisting of one SCWP-(carbohydrate)part and a functional molecular part, the carbohydrate part can consist of an intact SCWP, partial structures (oligosaccharids fragments) made from SCWP by chemical breakdown or synthetically manufactured partial structures of the SCWP (oligosaccharide derivatives).

The functional molecular part can have the function of being a bond to lipid phases (for example, liposomes) or gold, a secure anchor to a solid phase (for example, S-layer), polymerization capacity (the constructed conjugate acts as a co-monomer), pharmaceutical effect, combined function such as bonding to lipid phases and immuno-stimulated effect (lipid-A-derivative, type FK-565 lipopeptide) or, finally, detectability (e.g., fluorescence).

Chemically, the linking of the carbohydrate part with the functional part can occur in various ways, namely:
Reductive amination (formation of Schiff's bases with subsequent reduction to secondary amines).
Thiocarbamide formation or
Amide formation.

The reductive amination can occur on the carbonyl components of the carbohydrate part through the dissociation of the reduced phosphoric acid residue from the SCWP with the formation of reduced SCWPs, through partial De-N-acetylization and desaminization with nitrous acids with the formation of anhydromannose (anhydroglucose?) end groups, through β-elimination of SCWP containing uronic acid, or through breakdown of periodate (possible partial breakdown). The reductive amination can be carried out on the functional part of the amino components by using ehtylenediamine, propolenediamine or by introducing an amino group on the reduced end of the SCWP by using allylamine, aminomethacrylic acid and its derivatives, other amino compounds with unsaturated groups (Aldrich catalog) or S-layers (ε-lysin-$NH_2$ groups). A carbonyl component reacting with ethylenediamine or another diamine compound can result in amino groups on the carbohydrate part. The carbonyl components on the functional part can acquire a Smith product of S-layers or polysaccharides.

The thiocarbamide can form through FITC (fluorescein isothiocyanate) or through the conversion of primary amines in isothiocyanate through reaction with thiophosgenes.

The amine formation can occur on the carbonic acid part of the carbohydrate (SCWP) through lactal-lactone bromoxidation, on the amino components similar to reductive amination, on the amino components of the carbohydrate (SCWP) through the formation and reaction of a carbonyl component with ethelenediamine or another diamine compound, and on the carbonic acid part of the functional molecule as activator or long-chained fatty acids and branched fatty acids, as activator of asparagus acid or lipoic acid as well as activator of methacrylic acid (derivatives) and other unsaturated carbonic acids.

EXAMPLES

Group 1: Modification of Secondary Cell Wall Polymers

The secondary cell wall polymers (SCWP) were extracted from peptidoglycan-containing Sacculi of various Bacillaceae by using 48% hydrogen fluoride (HF) based on the specifications of von Ries, et al (1997), cleaned by gel filtration chromatography, the eluates dialyzed against A. purify., the inner dialysate frozen at −20° C. and lyophilisated. The organisms used whose S-layer proteins and SCWP have the following name: *Bacillus stearothermophilus* PV72/p6 (Sára et al, 1996), SbsA (Kuen et al, 1994), type A SCWP (Egelseer et al, 1998); *Bacillus stearothermophilus* ATCC 12980 (Egelseer et al, 1996), SbsC (jarosch et al, 2000), type A SCWP 9Egelseer et all, 1998); *B. stearothermophilus* PV72/p2 (Sára et al, 1996), SBsB (Kuen et al, 1997), type B SCWP (Ries et al, 1997; Sára et al, 1998); *B. spaericus* CCM 2177 (Sára et al, 1989), SbpA, type C SCWP (Ilk et al, 1999); *Thermoanaerobacter thermohydro-*

*sulfuricus* L111-69 (Sára et al, 1988); Stta, type D SCWP. An exact listing of the properties of the individual S-layers and the corresponding SCWP can be found in Table 1.

polymer chains can be determined from the ratio of the glocosamine to the leucine. For all SCWPs, this was found to be >95%.

TABLE 1

| Organism | 1. S-layer protein<br>2. Lattice type<br>3. Overall length<br>4. Signal peptide | Genbank accession number | SCWP | Main components of the SCWP/ maximum MG | Interaction of the SCWP with the |
|---|---|---|---|---|---|
| *Bacillus stearothermophilus* PV72/p6 | SbsA<br>hexagonal<br>1 228<br>30 | X 71092 | Type A | Glucose:N-acetyl-glucosamine:2,3-dideoxy-2,3-diacetamidomannuronic acid = 1:1:2; structure clarified ($MG_{max}$ 50,000) | N-terminus (AS 31-257 no SLH motifs) |
| *Bacillus stearothermophilus* ATCC 12980 | SbsC<br>oblique<br>1 099<br>30 | AF055578 | Type A | same as above | N-terminus (AS 31-257 no SLH motifs) |
| *B. stearothermophilus* Mut 1 | SbaD<br>oblique<br>940<br>30 | AF228338 | Type A | same as above | N-terminus (AS 31-257 no SLH motifs) |
| *Bacillus stearothermophilus* PV72/p2 | SbsB<br>oblique<br>920<br>31 | X 98095 | Type B | N-acetyl-glucosamine:N-acetyl-mannosamine = 2:1; negatively loaded by pyruvate ketal, glycerine and uroic acid available; very complex configuration; structure not yet completely clarified ($MG_{max}$ 24,000) | N-terminus (3 SLH motifs; AS 33-204) |
| *B. spaericus* CCM 2177 | SbpA<br>cube<br>1 322<br>30 | AF211170 | Type C | N-acetyl-glucosamine:N-acetyl-mannosamine = 2:1; each $2^{nd}$ N-acetylmannosamine has a pyruvate ketal; structure clarified ($MG_{max}$ 10,000) | N-terminus (3 SLH motifs; AS 33-202) |
| *Th. thermohydrosulfuricus* L111-69 | SttA<br>hexagonal<br>unknown | none | Type D | N-acetyl-glucosamine:N-acetyl-mannosamine:Mannose = 1:0.5:1; loaded negatively with pyruvate ketal; structure not yet clarified ($MG_{max}$ ~25,000) | N-terminus |

Example 1

Conversion of Latent Aldehyde Groups (Reduced Ends) of the Polymer Chains in Free Amino Groups To modify the reduced ends (latent aldehyde groups) of the type A, B, C and D SCWP, the following steps were performed: 10 mg of lyophilisated material were dissolved in 2 ml of saturated carbazole/hydrazide solution (pH 6.2). Then 200 µl of sodium cyanoborohydride (NaBH3CN; 20 mg/ml A. purify.) were added, 15 minutes at 100° C., then incubated for 16 h at 90° C. To remove surplus reagents, it was dialyzed for 24 h against A. purif., the samples frozen at −20° C. and lyophilisated. To determine the free amino groups, 1 mg of the respective SCWP was dissolved in 2 ml of 50 mM sodium hydrogen carbonate buffer (pH 7.8), and 100 µl of a solution butyloxycarbonyl-L-leucine-N-hydroxysuccinimide ester (BOC Leuse; 3.5 mg/ml 100% ethanol) added. The reaction batch was stirred for 18 h at 20° C., then for 6 h against a mixture of ethanol—A. purif., (30:7/v:v) and then dialyzed against A. purif. The inner dialysate was then lyophilisated and 0.5 mg of the lyophilisated material hydrolyzed with 6 N HCl for 6 h at 110° C. for the amino acid and amino sugar analysis (BIOTRONIK amino acid analyzer; Maintal, D.). The degree of modification of the Example 2

Conversion of the Amino Groups Introduced in the SCWP into Thiole Groups

To convert the amino acids introduced in the SCWP, 5 mg of the SCWP modified according to Example 1 was dissolved in 5 ml of 0.25 M triethanolamine-HCl buffer (pH 8.5). After adding 4 mg of 2-iminothiolane (4-mercaptobutyrimidate), the solution was incubated for 2 h at 37° C. under a nitrogen atmosphere, and finally dialyzed for 18 h at 4° C. against degassed A. purif. to remove the reagents. The inner dialysate was then frozen and lyophilisated. The number of thiole groups introduced was determined according to the Ellman method (1959). It was shown that the amino groups could be converted quantitatively into thiole groups.

Example 3

Modification of Introduced Amino Groups Using Blotin

To modify the free amino groups (see Example 1), 5 mg of type A, B, C or D lyophilisated SCWP were dissolved in 20 mM of potassium-phosphate buffer (pH 7.8) and 0.5 mg of sulfo-NHS-biotin (sigma) added. The modification happened following the instruction recommended by the company Pierce. To remove surplus reagents, it was dialyzed for 18 h at 4° C. against A. purif., the inner dialysate frozen at −20° C. and lyophilisated.

Example 4

Activation of the Freely Introduced Amino Groups

To activate the introduced amino groups, 5 mg of the lyophilisate from Example 1 was dissolved in 500 µl of of p-phenylenediamine (10 mg/ml A. purif.). Then 100 µl of $NaBH_3CN$ solution (20 mg/ml A. purif.) was added, 15 min. at 100° C., then incubated for 16 h at 90° C. The reagents were then removed against A. purif. or, selectively, by cleansing using a Superdex S75 column (Pharmacia, Uppsala, Sweden) with 0.1 M TRIS-HCl buffer (pH 7.8) as solvent. The diazotization of the amino groups introduced in the SCWPs was done using $NaNO_2/HCl$ following the method described by Manjon (1985). For the diazotization, 5 mg of p-phenylenediamine modified SCWP was stirred at 4° C. in 35 µl of of a precooled mixture of 2 parts $NaNO_2$ solution (4$ in A. purif.) and 5 parts 2 N HCl, and the solution with the diazotized SCWP immediately brought into contact with the substances that contained the free amino groups.

Example 5

Detecting Biological Activity of HF-Extracted, Native and Chemically Modified SCWP To detect the specific bonding between the S-layer proteins indicated in the introduction and the various types of SCWPs, the surface plasmon resonance technique (SPR) was utilized (BIACORE 2000, Biacore, Uppsala, Sweden). The S-layer proteins were immobilized in aqueous form as unassembled monomers and/or oligomers in a concentration of 100 µl/ml A. purif. on pre-activated carboxy-dextran gold chips. The resonance units showed that about 70% of the surface of the chips were coated with S-layer proteins, where the method used resulting in the immobilization of the sub-units in static alignment. As an example, the studies with the S-layer protein SbsB of *B. stearothermophillus* PV72/p2, the S-layer protein recombinantly made in *Escherichia coli* (r $SbsB_{32-920}$; corresponding to pure SbsB of the wild type strain) and an N-terminal shortened form (r $SbsB_{206-920}$; the three SLH motifs are missing) were represented. Because of the adsorption curves, it was shown that the SbsB and r SbsB type B SCWP (concentration range 1–100 µl/ml 50 mM TRIS-HCl buffer, pH 7.2) immobilized on the chips are specifically detected;

R $SbsB_{258-920}$ (=Δ3 SLH motifs) immobilized on the chips have no affinity to type B SCWP;

SbsB and r SbsB32-920 immobilized on the chips had a comparable affinity for the type B SCWP that was modified in Example 1–4 as for the native type B SCWP;

SbsB and HF-extracted r SbsB32-920 immobilized on the chips do not bind with lysozyme-digested peptidoglycan.

Comparative tests were also made with the S-layer proteins SbsA, SbsC and r $SbS_{31-1099}$ and the type A SCWP, as well as SbpA, r SbpA and the type C SCWP and SttA and the type D SCWP. In all cases, conclusive proof of the specific bonding between the respective S-layer protein and the associated SCWP could be demonstrated.

Examples from Group 2: Bonding of Modified SCWPs to Molecules of a Solid Support for the Directed Monomolecular Bonding of S-Layer Proteins

Example 6

Using Micro-Filtration Membranes (MF) as Solid Support

An MF (Pall carboxydyne) with an average pore size of 0.4 µm and a diameter of 14 mm was used as support. To activate the free carboxyl groups, the MF was placed in a solution of EDC (10 mg/ml A. purif., pH 4.7) for 1 h at 20° C., and then washed three times with ice cold A. purif. For the covalent bonding of the type C SCWP, 5 mg of the modified material described in Example 1 was dissolved in 5 ml A. purif., where the pH value of the solution was set to 9.0 using 0.01 N NaOH. After 4 h of incubation at 20° C., the MF was removed and washed five times with 50 mM TRIS-HCl buffer (pH 7.2). Finally, the MF was placed in a solution of SpbA protein (100 µg/ml 10 nM $CaCl_2$ solution) and incubated for 6 h at 20° C. To remove the unbound S-layer protein the MF was washed five times with 10 ml 50 mM TRIS-HCl buffer (pH 7.2) and cut into 1 $mm^2$ large pieces which were extracted for 10 min at 100° C. with 100 µl of an SDS solution (sodium dodecylsufate; 10% in A. purif.). Consequently, 25 µl of the clear extract was mixed with 75 µl of the sample solution (Laemmli, 1971), and 1–10 µl of this mixture placed on an SDS gel (10% separation gel). Because of the strength of the protein bands of the sample (molecular weight of SpbA on the SDS gels—127, 000) and the comparison with corresponding SpbA standards, the amount on the bound S-layer protein was estimated at 80–100 $µg/cm^2$, which corresponds to the maximum bonding capacity of this highly porous MF for proteins indicated by the manufacturer.

Example 7

Using a Silicon Oxide Wafer (SOW) as Solid Support

3×5 mm SOW were incubated for 30 min in 500 µl of solution of aminosilane (5% in A. purif., pH 3.5) at 37° C. After fivefold washing with A. purif. and ethanol, the silanized SOW were dried for 15 min, then pre-activated for 2 h in a solution of m-Maleimidobenzoyl-N-hydroxysulfosuccinimide ester (Sulfo-MBS, Pierce; 150 µg/ml 0.1 M sodium-phosphate buffer, pH 7.0) at 37° C., and with washed with A. purif. To bind the modified type B SCWP (as described in Example 2), 1 mg of the lyophilisate/ml 0.1 M sodium-phosphate buffer (pH 7.0) was dissolved, and 500 µl applied to the SOW. After 2 h of incubation at 20° C. in an $N_2$ atmosphere, the little plates were washed with 0.1 M sodium-phosphate buffer and A. purif. For the directed bonding either SbsB or r SbsB (100 µg/ml 50 mM TRIS-HCl buffer, pH 7.2) was offered, and the SOW functionalized with type B SCWP incubated for 4 h in this solution at 20° C. Washing with TRIS-HCL buffer removed the excess S-layer proteins, examined the SOW in the AFM and the orientation of the oblique S-layer lattice determined. It was shown that SbSb and r SbsB had bonded with the inner side of the sub-units (N-terminal region that carries the 3 SLH motifs). From numerous studies on the SOWs it is known that SbsB binds with the outer side in the absence of type B SCWP (Neubauer et al, 2000). Consequently, the S-layer sub-units bonded to the SOW through the type B SCWP covalently bonded to the solid support. Instead of SbsB, recombinant SbSb streptavidin fusion protein can also be utilized.

Example 8

Using a Silicon Oxide Wafer (SOW) as Solid Support

For the introduction of thiole groups, a 3×5 mm SOW was placed for 30 min in a solution of 3-mercaptosilane (7% in 50% acetone) at 37° C. After fivefold washing with 50% acetone, the SOW was dried for 15 min. at 110° C. in an $N_2$ atmosphere. To activate thiole groups, 500 µl of a solution of 2–2' dipyridyldisulfide (5 mg/ml 10% ethanol) was applied to the SOW. The incubation time was 2 hours at 20° C. After the SOW was removed, it was washed several times with 10% ethanol and A. purif. and then incubated for 6 h in a 500 µl solution of type A SCWP (3 mg/ml A. purif., modified as described in Example 2) at 20° C. To remove surplus type A SCWP, the SOW was washed several times with A. purif., and 50 mM sodium-phosphate buffer (pH 7.0). For the directed bonding, the SOW loaded with type A SCWP was placed in a solution of the following S-layer protein forms (100 µg/ml 50 mM TRIS-HCl buffer, pH 7.2) for a period of 8 h: SbsC (wild type protein), r $SbsC_{31-1099}$ and r $SbsC_{342-1099}$. The N-terminal bonding region responsible for the type A SCWP (Jarosh et al, 2000) was lacking in the last two forms. The SOW was washed with TRIS-HCL buffer and A. purif. after the incubation with the various forms of S-layer protein forms and then examined in the AFM. Because of the oblique S-layer lattice comprising S-layer protein SbsC, a clear determination of the bonding side was possible. It was shown that the basic vectors had the same orientation as the intact cells or cell wall fragments of *B. stearothermophilus* ATCC 12980. In the event of N-terminal shortened r SbsC forms, no lattice structure could be discovered in the AFM.

Example 9

Using MF as Solid Support

The type A SCWP modified as in Example 1 was bonded to MF activated with carbodiimide (see Example 6). The following forms of SbsC were offered in a concentration of 150 µg/ml 50 mM TRIS-HCl buffer (pH 7.2), and the membrane wafers with a diameter of 14 mm incubated for 8 h at 20° C.: $SbsC_{31-1099}$, $SbsC_{258-1009}$, r $SbsC_{342-1099}$, r $SbsC_{31-844}$, r $SbsC_{31-860}$, r $SbsC_{31-880}$, r $SbsC_{31-900}$, r $SbsC_{31-920}$ and SbsC. After the incubation the MF was washed with 50 mM TRIS-HCl buffer (pH 7.2), cut into 1 mm² sections, extracted with SDS solution and examined with SDS-PAGE (see Example 6). Because of the respective standard series, the bonded amounts on those forms that carried the complete N-terminus could be estimated between 80–100 µg/cm². On the other hand, no bonding to the MF functionalized with type A SCWP took place with r $SbsC_{258-1099}$ and r $SbsC_{342-1099}$. The use of various shortened forms confirmed the results of the affinity studies (Egelseer et al, 1998; Jarosch et al, 2000) and the SPR measurements that only the N-terminus is responsible for the interaction with the SCWP.

Examples from Group 3: Synthesis of Glyco-Lipids (GL) from SCWPs

Example 10

GLs from All Types of SCPWs

The lyophilisated native SCPWS were dissolved in A. purif. (10 mg/ml A. purif.) and mixed with a solution of dipalmitoyl phosphatidyl ethanolamine (DPPE; 20 mg/40 µl chloroform: methanol=1:1). After incubation in screwed reaction tubes at 60° C. for a period of 4 h, $NaBH_3CN$ was added to the solution, and the incubation continued for 16 h at 60° C. The GLs formed were cleaned gel filtration chromatography (Superdex S75). The column eluate was examined for glucosamine and phosphate; every fraction that contained both components were cleaned and lyophilisated.

Example 11

GLs from All Types of SCWPs

Instead of the SCWP with reduced end, the SCPWs modified as in Example 2 were used with a free thiole group. DPPE was used as lipid components. To activate the SCWPs, 5 mg were dissolved respectively in 1 ml 50 mM sodium-phosphate buffer (pH 7.0), and 1 mg sulfo-MBS added. After incubation for 2 h at 37° C., the reactive mixture was mixed with a solution of DPPE (3 mg in 500 µl chloroform:methanol—1:1=v:v0, and the batch incubated for 16 h at 20° C. by stirring. In the same manner as in Example 10, the GLs were cleaned using gel filtration chromatography with the help of a Superdex S75 column.

Examples from Group 4: Using GLs for Making Liposomes and for the Directed Bonding of S-Layer proteins

Example 12

Proof of the Inclusion of GLs in Liposomes

Liposomes which contained DPPC, cholesterine and GL, as described in Example 10 or 11, from type C SCWP at a molecular ratio of 10:5:4 were made according to the methods described by Mader et al (1999) and cleaned of the output components using gel chromatography. To prove whether the hydrophilic chains of type B SCWP were exposed on the surface of the liposomes, a periodate oxidation was performed where only the vicinal hydroxyl groups were touched. The liposomes that were used for the reaction corresponded to a DPPC concentration of 2 µmol/ml 0.2 M sodium-acetate buffer (pH 4.5). As much sodium periodate was added to this suspension that a final concentration of 20 mM was reached. The reactive mixture was incubated by stirring for 1 h in the dark at 20° C. After the liposomes were centrifuged and washed twice with 0.2 M sodium hydrogen carbonate solution (pH 8.2), there were incubated for 4 h in a solution of ferritin (1 mg/ml 0.2 M sodium hydrogen carbonate, ph 8.2) at 20° C. For tests in the transmission electron miscroscope, the samples were negatively contrasted and embedded for ultra-thin cuts. The negatively contrasted preparation showed that the liposome surface was completely covered with ferritin; in the ultra-thin cut, a monolayer of ferritin could be seen on the liposome surface. After periodate oxidation, the type B SCWP was no longer biologically active; the free aldehyde groups could, however, be used for the covalent bonding of the foreign molecules with the exposed amino groups.

Example 13

Directed Recrystallization of the S-Layer Protein SbsB

The liposomes described in Example 12, containing the GL from DPPE and type B SCWP (see Example 10) were used for the directed recrystallization of the S-layer protein SbsB. SbsB bonded with the outer side of liposomes containing DPPE and cholesterol so that the N-terminus is aligned with the bonding regions for the type B SCWP in the external milieu (Mader et al, 1999). In case of the liposomes containing the GL from DPPE and type B SCWP, 2 ml of a suspension with a total DPPE content of 4 µmol was incubated for 6 h with 2 ml of an SbsB solution (1 mg/ml 50 mM TRIS-HCl buffer, pH 7.2) at 20° C., the suspension centrifuged to remove surplus S-layer proteins, the liposomes washed with 50 mM TRIS-HCl buffer (pH 7.2), and the preparation examined in the transmission electron microscope after freeze-drying at −80° C. and oblique shading with Pt/C. It was shown that in the case of the GL-containing liposomes the smooth outer side of the oblique S-layer lattice was exposed, while with the DPPE-cholesterol liposomes the rough inner side was recognized.

Example 14

Modification of DPPC/cholesterol/HAD-Containing Liposomes with SCWP

Liposomes were made as described by Mader et al (1999). The type C SCWP described in Example 1 and modified with 2-iminothiolan was used to functionalize the liposome surface. For this reason, the liposomes that corresponded to a DPPC concentration of 5 µmol was suspended in 3 ml 0.2 M sodium phosphate buffer (pH 7.0), and 2 mg sulfo-MBS was added to it to activate the free amino groups of HDA. After two hours of incubation at 20° C., it was centrifuged, the liposomes suspended in 2 ml of solution of type C SCWP (1.5 mg/ml sodium phosphate buffer, pH 7.0, modified according to Example 2), and incubated for 18 h at 20° C. Proving the immobilization of the SCWP, just like in Example 12, was done through periodate oxidation and immobilization of ferritin. The recrystallization of the S-layer protein, SbpA, was done in a similar manner was the procedure described in Example 13. The proof of the directed bonding of the SbpA protein was done using an electron microscope on the freeze-dried preparations damped with Pt/C.

Example 15

Using the r SbsB-Streptavidin Fusion Protein

A C-terminal SbsB-streptavidin fusion protein (4 mg lyophilisate) recombinantly prepared in E. coli was dissolved in 2 ml 6 M guanidinhydrochloride in 50 mM TRIS-HCl buffer (pH 7.2), 0.8 mg of streptavidin added and the solution dialyzed for 1 h at 20° C. against A. purif. After removal of the inner dialysate, it was centrifuged at 40,0000×g, and the clear protrusion that contained the soluble r SbsB-strept(4) was placed in a protein concentration of 120 µg/ml 0.2 TRIS-HCl buffer (pH 7.2). 1 ml of the protein solution was then mixed with 1 ml of the liposome suspension that was made as in Example 13, and the sample incubated for 2 h at 20° C. After the centrifuging, the liposomes were washed twice with 0.2 M TRIS-HCl buffer (pH 7.2), then incubated with biotinylated human IgC and the bond examined following the instructions developed by Mader et al (2000). A bonding of biotinylated human IgC was possible only because of the streptavidin residue exposed on the outside of the S-layer. The desired orientation (bonding through the N-terminus lying over the inside of the S-layer) was observed only for those liposomes where the type B SCWP was bonded covalently to the HDA.

Examples from Group 5: Layout of Lipid Bilayers

Example 16

Lipid Bilayers with Channel Protein with a Silicon Wafer as Solid Support

Thiole groups were introduced on one SOW (3×5 mm) through silanization with mercaptosilane (see Example 8). Modified type A SCWP (1 mg/ml 50 mM potassium phosphate buffer, pH 7.0) was bound to these thiole groups using sulfo-MBS as a heterobifunctional cross-linker just like in Example 1. After thorough washing of the SOW with phosphate buffer and A. purif., 500 µl of a solution of SbsA protein (100 µg/ml 50 mM TRIS-HCl buffer, pH 7.2) was applied, incubated for 6 h at 20° C., washed with buffer, and the SbsA protein with glutaraldehyde available as monolayer (0.5% in 50 mM potassium phosphate buffer, pH 7.2) cross-linked for 20 min at 20° C. A bilyaer of DPPE was then applied according to the method described by Schuster et al (1998), where α-haemolysin or valinomycin was inserted (Schuster et al, 1998 a, b).

Example 17

Using an S-Layer Ultra-Filtration Membrane (SUM) as Solid Support

An SUM wafer (diameter 25 mm) was placed in a ultra-filtration cell so that the outer S-layer was exposed. The free carboxyl groups of the S-layer protein were activated for 80 min at 20° C. by the addition of an EDC solution (6 mg/ml A. purify.; pH 4.7), the membrane surface washed three times with ice-cold A. purif., and then 2 ml of a solution of the type A SCWP modified as in Example 1 (1 mg/ml; pH 9.0) was applied for the covalent bonding to the S-layer outer side. After 5 h of incubation at 20° C., the SUM was washed three times with 50 mM TRIS-HCl buffer (pH 7.2) and three times with A. purif., and then incubated for 5 h with a solution of SbsA protein (100 µg/ml 50 mM TRIS-HCl buffer, pH 7.2) at 20° C. After the washing of the membrane wafer with buffer, a part was crushed and extracted using SDS solution by means of SDS-PAGE to examine the amount of bonded SbsA. An SbsA-SCWP SUM made in parallel was cross-linked with glutaraldehyde to stabilize the S-layer protein (as described in Example 16), and used to coat with a DPPE filme and integral membrane proteins (e.g., α-hameolysin).

Example 18

Covalent Bonding of a GL to an SUM

Using an SUM and coating with the GL from type C SCWP and DPPE described in Example 10 or 11. Consequently, the SUM functionalized with type C SCWP was incubated for 6 h with a solution of SbpA protein (50 µg/ml mM CaCl$_2$) at 20° C., and the SUM surface with 10 mM CaCl$_2$ solution washed thoroughly. To test the directed monomolecular bonding of the SbpA protein, the SUM was subjected to examinations under the transmission electron microscope and freeze-drying, and used for ultra-thin cuts. It was shown that a closed monomolecular layer with a cubic lattice was present, and the smooth outer side of the S-layer lattice was exposed.

Examples from Group 6: Making SCWP-Containing Copolymers

Example 19

Making a Copolymer by Using Acrylamide

A solution containing 20 mg of type C SCWP modified according to Example 1, 6.8 mg acrylamide and 3 µl N,N,N'N'-tetramethylethlenediamine per ml of A. purif. is degassed for 30 min. in a water jet vacuum. After adding ammonium peroxydisulfate (1 mg), it is left to react for 18 h at 4° C. Finally, the product is separated using a Sephadex G-50 92.6×100 cm, 0.01 M sodium hydrogen carbonate), desalinated using a Biogel P2 and lyophilisated. The SCWP content is determined by amino sugar analysis.

Example 20

Making a Copolymer by Using Polyvinyl Alcohol

A solution of polyvinyl alcohol (PVA; 3% in A. purif.) is made and 20 mg of native type A SCPW are added to 1 ml of this solution. Finally, 100 µl are poured out onto a clean container and dried for 30 minutes at 37° C. to stabilize the film. Alternatively, the film can be chemically solidified by incubation for 10 minutes in a solution of glutaraldehyde (0.5% in 0.1 M sodium phosphate buffer, pH 7.2). The PVA-SCWP film washed with A. purif. is used as a matrix for the directed recrystallization of the S-layer protein, SbsC (see Examples 8 and 9).

The invention claimed is:

1. A method for constructing a compound body through the use of bacterial secondary cell wall polymers as bonding agent, said method comprising:
    (a) bringing said polymers into contact with a support in solution, such that a first complex is formed; and then
    (b) bringing said complex into contact with a monomolecular lattice, such that a compound body is formed, comprised of said lattice and said complex.

2. A method according to claim 1, wherein said lattice has a first surface that presents secondary cell wall polymer-binding domains.

3. A method according to claim 2, wherein said lattice has a second surface that presents at least one protein comprised of a domain that functionalizes said compound body.

4. A method according to claim 1, wherein said polymers and said support are covalently linked.

5. A method according to claim 1, wherein said lattice is comprised of crystalline bacterial cell surface layer proteins.

6. A method according to claim 1, wherein said support is a micro-filtration membrane.

7. A method according to claim 1, wherein said support is a cell surface layer ultra-filtration membrane.

8. A method according to claim 7, wherein said lattice is a lipid layer.

9. A method for constructing a sandwiched compound body through the use of bacterial secondary cell wall polymers, said method comprising:
    (a) bringing said polymers into contact with crystalline bacterial cell surface layer proteins, such that a monomolecular crystalline protein layer is formed;
    (b) bringing said protein layer into contact with a lipid layer, such that said lipid layer is bound to said protein layer through said polymers to form a first aggregate compound body;
    (c) repeating steps (a) and (b) to form a second aggregate compound body;
    (d) bringing said first aggregate compound body into contact with said second aggregate compound body, such that said aggregate compound bodies bind to each other through the lipid layers to form a sandwiched compound body.

10. A method according to claim 9, wherein the protein layer of said first aggregate compound body is attached to a support.

11. A method according to claim 9, wherein said first and second aggregate compound body are comprised of different bacterial cell surface layer proteins.

12. A method according to claim 9, wherein said support is a micro-filtration membrane.

13. A method according to claim 9, wherein said support is a cell surface layer ultra-filtration membrane.

14. A method according to claim 8, wherein said monomolecular lattice is in the form of a liposome.

15. A method according to claim 1, wherein said support is a micelle comprised of hydrophobic self-assembling chains.

* * * * *